Figure 1:
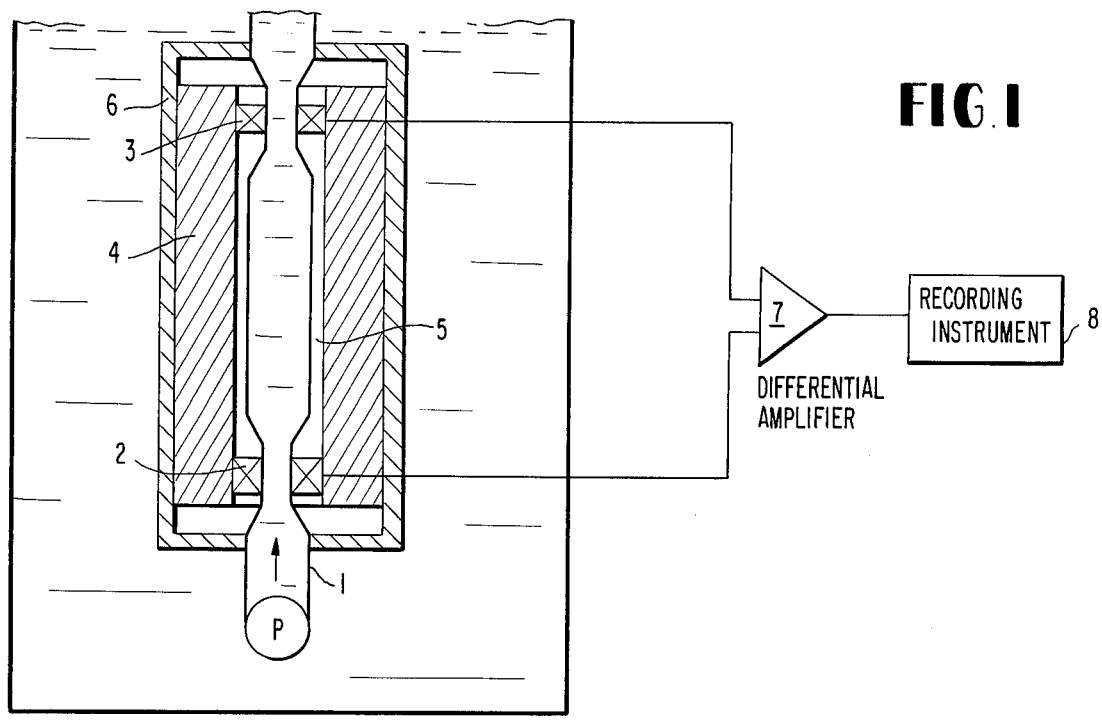

United States Patent

Wegstedt et al.

[11] 4,054,056
[45] Oct. 18, 1977

[54] CALORIMETRY PROBE

[75] Inventors: Lars Wegstedt, Jarfalla; Bengt Lindblad, Spanga, both of Sweden

[73] Assignee: LKB-Produkter AB, Bromma, Sweden

[21] Appl. No.: 638,543

[22] Filed: Dec. 8, 1975

[30] Foreign Application Priority Data

Dec. 12, 1974 Sweden .................. 7415590

[51] Int. Cl.² ............... G01K 17/00; G01N 33/00
[52] U.S. Cl. .......................... 73/190 R; 23/253 R; 195/127
[58] Field of Search ............. 73/15 B, 190 R; 23/253 R, 254 E; 195/127

[56] References Cited

U.S. PATENT DOCUMENTS

| 2,393,362 | 1/1946 | Gerhold | 23/254 |
| 3,436,190 | 4/1969 | Priestley et al. | 73/190 X |
| 3,467,501 | 9/1969 | Groszek | 73/190 X |
| 3,524,340 | 8/1970 | Kocherzhinsky | 73/15 |
| 3,552,207 | 1/1971 | Monk et al. | 73/53 |
| 3,578,405 | 5/1971 | Woodle | 73/190 |
| 3,740,194 | 6/1973 | Hendy | 73/15 |

Primary Examiner—Herbert Goldstein
Attorney, Agent, or Firm—George H. Mitchell, Jr.

[57] ABSTRACT

A calorimetric probe for measuring heat produced in a fluid consists of a tube through which the measured fluid flows and having two thermoelements at intervals spaced along the tube, each being connected between the tube and a surrounding element having good heat transmitting qualities, the surrounding element itself being separated from the first tube by a column of air so that a comparison of the readings of the two thermoelements provides a measure of heat developed in the liquid while passing between the two thermoelements.

4 Claims, 2 Drawing Figures

CALORIMETRY PROBE

The present invention refers to a calorimetry probe to be introduced into a heat developing fluid.

The parameters commonly used for continuous control of fermentation processes have their special limitations which decrease the possibility of their general application. Thus turbidimitry gives uncertain results at high cell concentrations and furthermore the measuring is affected by the turbidity of the nutrition medium which can vary during the process of fermentation. Measuring of dissolved oxygen gives correct information only during a limited period in aerobic fermentation. A measurement of the consumption of alkali, oxygen consumption or carbon monoxide production all give a certain information but the measurements are not directly related to the growth but vary heavily under different conditions of growth.

Calorimetry is a method well suited for continuous survey of fermentation. The direct measuring of the heat effect is through its derivating character superior to for instance determination of dried cell weight or turbidimitry, especially at fast metabolic changes in the fermentation process. The heat production of the culture is directly related to the energy metabolism and measuring with calorimetric methods can therefore be applied to aerobe as well as anaerobic processes.

The requirement for industrial application of calorimetry is that the measuring should be possible to carry out in reaction tanks of very different volumes. In big fermentors the cooling effect has been used as a measure of the heat development. This method for measuring is, however, very coarse and too slow to be used for control purposes.

Flow calorimetry offers many advantages but has also certain disadvantages when applied to microbiological systems. Substantial advantages consist therein that a flow calorimeter can be designed for very accurate measurement and is independent of the volume of the fermentation tank. A draw-back is that the culture could change its metabolism and thus its heat production during transport to the measuring cell. In order to diminish the influence of the transport to the cell it is thus desirable to use a type of calorimeter which has a very short flow path. Commercially available flow calorimeters, however, usually have a very long flow path because of the requirements of accurate tempering with a heat exchanger arranged in front of the measuring cell. An example of such flow calorimeter is described for instance in the Swedish patent 329,025.

It is an object of the present invention to provide a calorimetry probe which can be immersed into a fluid and which has a short flow path and wherein the surrounding fermentation liquids could be used as a heat exchanger and a heat sink. The characteristics of the invention will appear from the claims attached to the specification.

Figure 2:
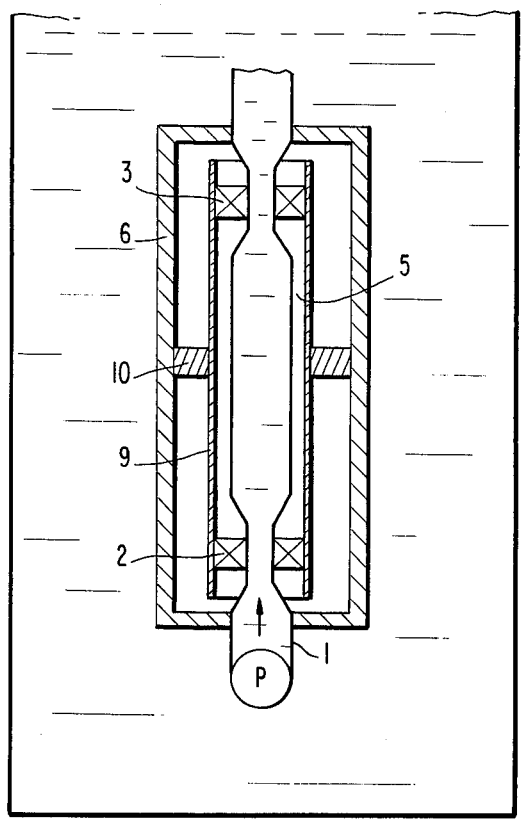

The invention will now be described in detail reference being made to the enclosed drawing in which:

FIG. 1 schematically shows a sectional view through a first embodiment of a calorimetric probe of the invention; and FIG. 2 in a corresponding way shows a section of a second embodiment of the invention.

In FIG. 1 which shows a section through a calorimetric probe according to the invention to be immersed into a liquid tank not shown in the figure, reference 1 denotes a tube through which the liquid of the surrounding tank is made to flow, for instance by means of a pump not shown in the figure. The tube is surrounded by a protecting cover 6, made for instance by stainless steel. Within the cover at a certain distance from each other two thermoelements 2 and 3 are coupled to the tube, one side of each of the thermoelements being connected to the tube and the other side being connected to an aluminium cylinder 4 which surrounds the tube and is in contact with the cover 6 but which leaves a narrow isolating air slot 5 between the cylinder and the tube. Both thermoelements 2 and 3 are connected to a differential amplifier 7, the output of which is connected to a recording instrument 8.

The above described calorimetry probe works as follows: Fermentation fluid flows from below through the tube and at the first thermoelement 2 the temperature difference between the fluid and the surrounding aluminium cylinder is measured. The liquid then flows on through the tube which after passing the first thermoelement is thermally isolated from the surroundings by means of the air slot between the tube and the surrounding block. The heat generated by the microorganisms can now not be dissipated but will instead raise the temperature of the liquid. At the next thermoelement the temperature difference between the liquid and the surrounding block is again measured. The measuring signals from both thermoelements are compared in the differential amplifier and the difference between the signals constitutes a measure of the temperature rise of the liquid at the passage between the measuring points and thus constitutes a measure of the activity of the microorganisms.

One of the problems in this type of measurements consists therein that temperature cannot be maintained equal in all parts of the liquid volume and also the temperature of the liquid volume as a whole could vary somewhat. This give rise to a recording curve with oscillations around a mean value. The recording will thus be difficult to evaluate and it will be necessary to have a signal treatment that compensates from the fast oscillations. Such a signal treatment could suitably be performed in one of the three following ways:

1. Low pass filtration, the draw-back of such filtration consisting in that single big disturbances will affect the recording during a long time.
2. Delay of the signal from the first measuring point with the same time as is required for the liquid to pass from measuring point 1 to measuring point 2. The disturbance at the first measuring point will then be compensated by an equal disturbance at the point 2.
3. cyclical integration, whereby the integration is performed during predetermined periods of time, the integrated value at the end of each period being transferred to a memory, the level of which is registered by a recorder Another method for compensating the temperature variations of the liquid volume could be achieved by means of the probe shown in FIG. 2, in which figure parts common to FIG. 1 are denoted by the same symbols. In FIG. 2 the thick aluminium cylinder 4 has been replaced by a thin tube 9 made by some material with low heat capacity and a high thermal conductivity as for instance silver. This tube is thermally isolated from the surrounding cover all over its surface except for one point, namely at a contact ring 10 arranged between the tube and the cover.

An advantage with the design shown in FIG. 2 is that if the ring 10 is made displaceable it is possible to adjust the ring so as to make temperature changes in the surrounding fluid to reach both measuring points at the same time. Furthermore, both measuring points will be equally affected irrespective of what part of the outer cover that is reached by a temperature disturbance.

We claim:

1. Calorimetric probe for measuring exothermic reactions in a liquid, comprising a protective cover defining a hollow vessel to be immersed in heat exchanging relationship in a body of said liquid, an elongated tube in communication with said body of liquid and defining a flow path for said liquid, at least a portion of the length of said tube being contained within said protective cover in heat isolating relationship thereto, a pair of thermoelements and means thermally coupling each of said thermoelements between said protective cover and said elongated tube at respective locations spaced along the length of said heat isolated portion, each of said thermoelements being capable of measuring the temperature difference between the protective cover and the elongated tube at said respective spaced locations, whereby the exothermic heat produced during a flow of said liquid between said spaced locations can be measured.

2. Calorimetric probe according to claim 1, characterized in, that the thermoelements are thermally coupled to the cover via a cylinder surrounding the tube and having a high heat capacity made of a material such as aluminum, the outer surface of the cylinder being in contact with the cover and the inner surface of the cylinder being in contact only with the thermoelements.

3. Calorimetric probe according to claim 1, characterized in, that the thermoelements in addition to being coupled to the cover also are coupled to one another via a thin second tube surrounding the first tube and made of a material with a high heat conductivity such as silver, the inner surface of the second tube being in contact only with the thermoelements and its outer surface being in contact with the inner surface of a ring having its outer surface in contact with the cover.

4. Calorimetric probe according to claim 3, characterized in, that the ring is displaceable along the first tube.

* * * * *